United States Patent [19]

Lee et al.

[11] Patent Number: 4,946,555
[45] Date of Patent: Aug. 7, 1990

[54] APPARATUS AND METHOD FOR MEASURING VENT GAS FLOW RATES AND PARAMETERS IN PULP AND PAPER PROCESSING

[75] Inventors: Robert G. H. Lee, Montreal; Derek Hornsey, Beaconsfield; José Dieguez, St-Bruno, all of Canada; Arthur S. Perkins, Moraga, Calif.

[73] Assignee: Canadian Liquid Air Ltd./Air Liquide Canada, Montreal, Canada

[21] Appl. No.: 298,749

[22] Filed: Jan. 19, 1989

[51] Int. Cl.$^5$ .............................................. B21C 9/147
[52] U.S. Cl. ........................................ 162/49; 162/63; 162/65; 162/236; 162/DIG. 10; 162/DIG. 11; 73/25.03
[58] Field of Search ..................... 162/65, 49, 63, 263, 162/DIG. 10, DIG. 11; 73/25

[56] References Cited

U.S. PATENT DOCUMENTS

| | | | |
|---|---|---|---|
| 4,016,029 | 4/1977 | Samuelson | 162/63 |
| 4,050,981 | 9/1977 | Jamieson | 162/65 |
| 4,192,708 | 3/1980 | Bergstrom | 162/49 |
| 4,198,266 | 4/1980 | Kirk | 162/49 |
| 4,384,959 | 5/1983 | Bauer | 162/49 |
| 4,419,184 | 12/1983 | Backlund | 162/49 |
| 4,717,672 | 1/1988 | Fleming | 162/49 |
| 4,840,703 | 6/1989 | Malmsten | 162/65 |

OTHER PUBLICATIONS

"Optimizating oxygen extraction by vent gas analysis: process control and safety" by Cirucci, TAPPI Journal, Jul. 1986, pp. 94–97.

"Experience for hydrostatic medium–consistency oxygen delignification of Rauma Pulp Mill" by Kovasin and Malmsten, Pulp & Paper Canada, 88:8(1987), pp. 36–39.

Primary Examiner—David L. Lacey
Assistant Examiner—Thomas M. Lithgow
Attorney, Agent, or Firm—Oblon, Spivak, McClelland, Maier & Neustadt

[57] ABSTRACT

An inert gas such as helium is employed as a tracer gas in a pulp and paper mill to determine the utilization of oxygen by an aqueous cellulosic pulp particularly, as well as other parameters, in an oxygen delignification or extraction in which oxygen is dissolved in the pulp and reacted to solubilize lignins and reduce the requirement for chlorine-based bleaching chemicals.

6 Claims, 4 Drawing Sheets

APPARATUS AND METHOD FOR MEASURING VENT GAS FLOW RATES AND PARAMETERS IN PULP AND PAPER PROCESSING

BACKGROUND OF THE INVENTION (a) Field of the Invention

This invention relates to the treatment of aqueous cellulose pulp in the pulp and paper industry; more especially the invention is concerned with a method and apparatus for detecting gas parameters in such a treatment.

(b) Description of the Prior Art

The treatment of cellulose pulp in the manufacture of paper includes several stages; the later stages include chemical bleaching operations which typically employ chlorine-based chemicals, for example, chlorine dioxide and sodium hypochlorite. Such bleaching operations can be carried out under conditions in which very little of the lignin still remaining in the pulp fibres after earlier delignification stages is removed, as well as under conditions in which the delignification is substantially completed.

Consumption of chlorine-based chemicals in the bleaching of pulp is considerable and costly, additionally it produces chloro-organic compounds as side products which represent a disposal problem. Many of the chloro-organic compounds are of complex structure, not readily broken down and are potentially hazardous or in any event raise concerns as to their long term effect on the environment.

In order to reduce the consumption of chlorine-based chemicals in the bleaching operation, oxygen is used in oxygen delignification and oxygen extraction stages in the treatment of pulp, which stages precede the bleaching operation; in both the oxygen delignification and extraction stages delignification of the pulp fibres is achieved.

The oxygen delignification and oxygen extraction processes both involve dispersion of oxygen in the aqueous cellulosic pulp under pressure. The dispersed oxygen is absorbed and reacts as the pulp flows upwardly through a vertical reactor or retention tube. In the case of medium consistency pulp, which contains 8-12%, by weight, of cellulose solids, the dispersing of the oxygen in the pulp is achieved, for example, by means of a medium consistency mixer or a gas diffuser having a high velocity of pulp passing across it.

SUMMARY OF THE INVENTION

It is an object of this invention to provide a method of determining the oxygen gas consumption of an aqueous cellulosic pulp.

It is a further object of this invention to provide a method of determining a gas parameter during oxygen gas consumption by an aqueous cellulosic pulp, particularly a pulp containing entrained air.

It is still a further object of this invention to provide an apparatus for the treatment of aqueous cellulosic pulp in which it is possible to determine gas parameters such as oxygen gas consumption by the pulp.

In carrying out the oxygen delignification and oxygen extraction it would be advantageous to be able to measure or evaluate parameters such as the oxygen consumption, air entrainment by the pulp, channeling of the pulp and gas separation or channeling in the reactor. With such measurements it would be possible to evaluate the efficiency of oxygen consumption and related parameters could be determined.

In accordance with this invention there is provided a method in which a known flow rate of an inert gas is introduced into oxygen gas prior to dispersion in the pulp. The inert gas passes through the reactor without reaction and is liberated or vented from the reactor together with unreacted oxygen. By monitoring the inert gas and oxygen concentrations of the liberated or vented gases it is possible to determine the proportion of the oxygen which has been consumed, as well as other parameters.

Any inert gas can be used which is essentially insoluble in the aqueous cellulosic pulp, which will not react in the reactor and which can be distinguished from other gases such as oxygen and nitrogen in the vent gases. Advantageously, the inert gas should be one having a property or characteristic which readily distinguishes it from oxygen, nitrogen and air and based on which its concentration can be readily determined.

In this way the inert gas functions as a tracer gas whereby gas parameters can be monitored.

An especially preferred inert gas is helium, however, the other rare gases, for example, argon, and such insert species as silicon hexafluoride can also be used.

Helium is a chemically inert gas that is non-toxic and non-flammable. It has very low solubility in water as can be seen from Table (I):

TABLE (I)

| SOLUBILITY OF HELIUM IN WATER | | |
|---|---|---|
| TEMP. °C. | PARTIAL PRESS. 101.3 kPa | HELIUM GAS 3.0 kPa |
| 60 | 8.95 ccs/l | 0.27 ccs/l |
| 70 | 9.44 | 0.28 |
| 80 | 10.10 | 0.30 |

The low solubility, chemical inertness and absence of background traces in medium consistency pulp make helium a suitable tracer gas.

Helium has a much higher thermal conductivity than oxygen, nitrogen or air as can be seen from Table (II):

TABLE (II)

| THERMAL CONDUCTIVITY AT 300° K. | |
|---|---|
| GAS | THERMAL CONDUCT. cal cm$^{-1}$ s$^{-1}$ K$^{-1}$ |
| OXYGEN | 6.18 × 10$^{-5}$ |
| NITROGEN | 6.27 × 10$^{-5}$ |
| AIR | 6.29 × 10$^{-5}$ |
| HELIUM | 36.47 × 10$^{-5}$ |

This large difference in thermal conductivity enables helium to be easily distinguished in the presence of mixtures of oxygen, nitrogen, and air. This is readily accomplished by using a portable analyzer that measures changes in thermal conductivity.

BRIEF DESCRIPTION OF THE DRAWINGS

The invention is illustrated in particular and preferred embodiments by reference to the accompanying drawings in which.

DESCRIPTION OF PREFERRED EMBODIMENTS WITH REFERENCE TO THE DRAWINGS

Figure 1:
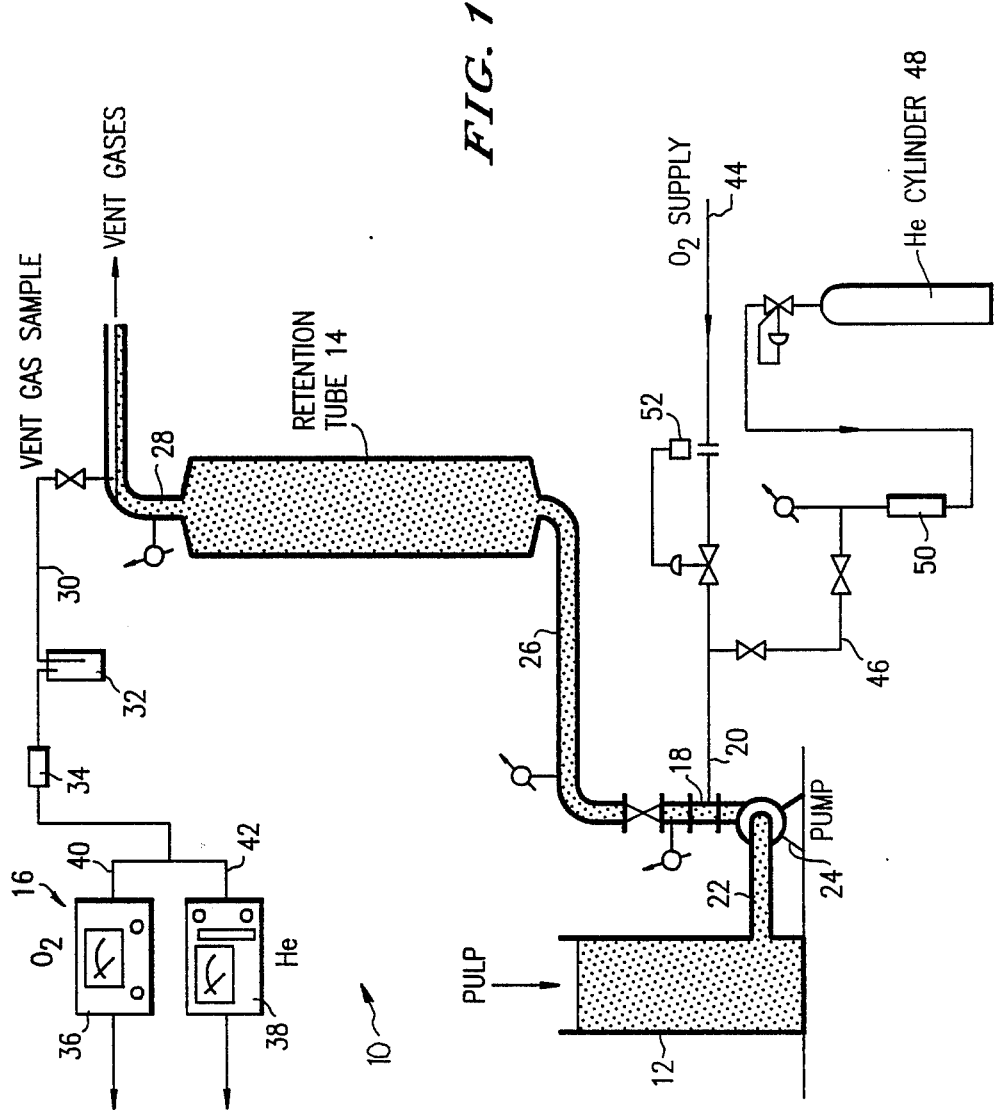
FIG. 1 illustrates schematically a system for the purposes of the present invention.

With further reference to FIG. 1 there is shown a system 10 having provision for detection of gas parameters during treatment of aqueous cellulose pulp with oxygen.

System 10 includes a pulp tank 12, a reaction column 14, a sampling assembly 16, an oxygen diffuser 18 and a gas supply line 20 for delivery of a mixture of oxygen, gas and helium.

A pump 24 is disposed in an outlet line 22 from pulp tank 12. Outlet line 22 communicates via pump 24 with a column inlet line 26 to reaction column 14.

Oxygen diffuser 18 is disposed in column inlet line 26 downstream of pump 24.

Reaction column 14 has a column oulet line 18 for flow of treated cellulosic pulp and vent gases and a sampling line 30 for vent gases communicates with outlet line 28.

Sampling line 30 includes a water trap 32 and a dryer 34.

Sampling assembly 16 includes an oxygen analyzer 36 and a helium analyzer 38. Sampling line 30 branches through lines 40 and 42 to analyzers 36 and 38 respectively.

Gas supply line 20 is connected to an oxygen line 44 connected to a source of oxygen (not shown). A device 52 for measurement and control of oxygen flow is disposed in line 44. Gas supply line 20 is further connected to a helium line 46 connected to a helium cylinder 48 as a source of helium. A calibrated rotometer 50 is disposed in helium line 46.

Gas supply line 20 communicates with oxygen diffuser 18 in column inlet line 26.

In operation an aqueous cellulosic pulp, for example, a medium consistency pulp having a solids content of 8 to 12% is pumped by pump 24 at a flow rate typically of the order of 100 cu.ft./min. from pulp tank 12 into reaction column 14 through outlet line 22 of pulp tank 12 and column inlet line 26. A continuous stream of oxygen gas under pressure is fed from a supply source (not shown) through oxygen line 44 into gas supply line 20. The flow rate of the oxygen in line 44 is measured and controlled by the device 52.

Conveniently the oxygen gas may be fed at a pressure and flow rate dependent on the character of the pulp and the pulp flow rate. In the case of the indicated medium consistency pulp and the indicated flow rate of 100 cu.ft./min., the oxygen will typically be fed at a pressure of 5 to 10 atmospheres and a flow rate to provide 10 lbs. $O_2$/ton of pulp.

A continuous stream of helium gas is fed from helium cylinder 48 through helium line 46 and into gas supply line 20. The flow rate of helium is measured by rotameter 50. Typically the helium is introduced to provide a concentration of about 1-4%, by volume, based on the joint stream of helium and oxygen in line 20.

The mixture of oxygen and helium enters the pulp in line 26 via oxygen diffuser 18 which serves to effect diffusion or dispersion of the oxygen into the aqueous pulp, whereby a proportion of the oxygen is dissolved in the aqueous pulp.

The aqueous pulp flowing to the base of reaction column 14 thus contains dissolved oxygen as well as undissolved oxygen and undissolved helium.

The dissolved oxygen reacts with the cellulosic pulp, more especially with the lignin, in reaction column 14 and during the passage of the aqueous pulp containing the dissolved oxygen vertically upwardly through reaction column 14.

In particular, the dissolved oxygen reacts with the lignin to produce addition products which are water soluble and thus pass into solution in the aqueous medium of the pulp or are readily removed from the pulp by subsequent washing stages downstream of reaction column 14.

The treated pulp together with vent gases comprising the undissolved oxygen and undissolved helium exit from an upper end of reaction column 14 via column outlet line 28, and a sample of the vent gases is withdrawn from line 28 through sampling line 30 to sampling assembly 16.

The vent gases in sampling line 30 are passed successively through a water trap 32 and dryer 34 to remove water and moisture entrained by the vent gases. Portions of the vent gases are thereafter fed through lines 40 and 42 to the oxygen analyzer 36 and the helium analyzer 38, respectively, by means of which the concentration of oxygen and concentration of helium in the vent gases are determined in known manner.

Typically, the gas pressure in reaction column 14 will be of the order of 0-20 psig at the top and 60 to 70 psig at the bottom.

It will be understood that oxygen gas is not readily soluble in water and thus oxygen diffuser 18 is necessary to effect dissolving of oxygen in the aqueous medium. Such diffusers are well known, however other devices for introducing oxygen may also be used, for example mixing devices such as that marketed as a Sunds medium consistency mixer. Desirably oxygen is dissolved in the aqueous medium to form a saturated solution since this maximizes the efficiency.

It will be understood too that in view of the relatively low solubility of oxygen in water, not all of the oxygen is dissolved, so that the cellulosic pulp flowing into column 14 will contain both dissolved and undissolved oxygen from the supply.

The sampling line 30 is conveniently located in outlet line 28 close to reaction column 14 to avoid aspiration of air into the sampling line 30 from the atmosphere.

The vent gas is discharged through sampling line 30, water droplets are separated in the water trap 32 and dryer 34 suitably contains a dessicant.

In introducing the helium in helium line 46 into the oxygen in oxygen line 44, the point of introduction of helium into the oxygen is chosen so that there is sufficient residence time for a complete mixing of the helium with the oxygen. The helium cylinder 48 suitably contains high purity helium gas and is equipped with a regulator to reduce the pressure to just above that of the oxygen in oxygen line 44. The helium is added to the oxygen at a known flow rate by passing it through calibrated rotometer 50. As the oxygen is introduced into the aqueous pulp at oxygen diffuser 18, it contains a predetermined fixed concentration of helium.

Thus the oxygen and helium are introduced at a known flow rate to the aqueous pulp and the concentration of oxygen and helium in the vent gas is determined by the sampling assembly 16.

Figure 2:
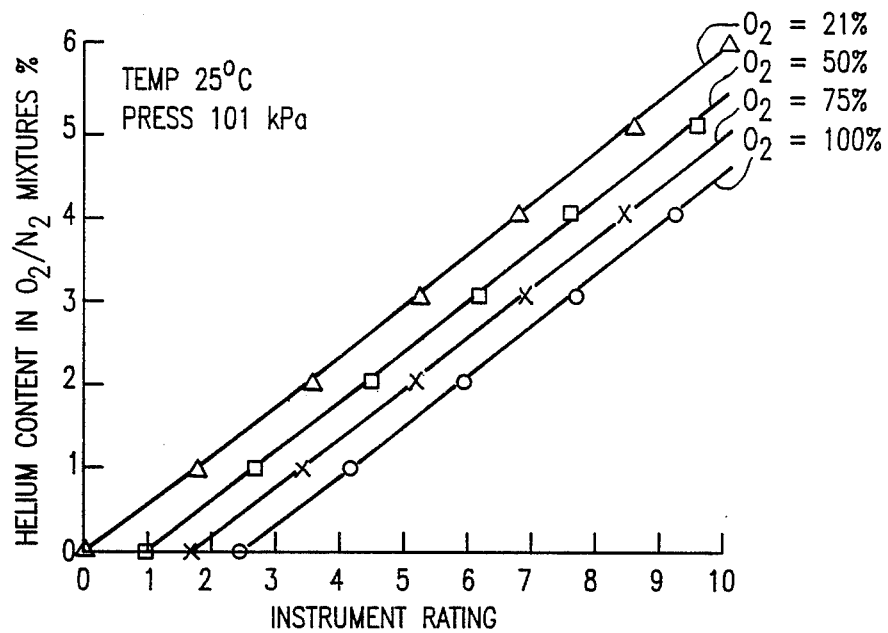
FIG. 2 shows graphically a calibration plot for a helium analyzer.

As a preliminary step the oxygen analyzer 36 and the helium analyzer 38 are calibrated. The helium analyzer 38 is calibrated against known mixtures of helium in air and oxygen enriched air on a dry gas basis. With reference to FIG. 2 there is shown a typical graph drawn up of helium concentration against the scale reading of the helium analyzer 38 for a helium concentration of 0 to 6%. A family of curves is obtained for different oxygen concentrations mixed with air and helium as identified in FIG. 2.

The oxygen analyzer 36 is zeroed using nitrogen gas, and calibrated using air and oxygen.

In carrying out the method of the invention, the system 10 is established with flow of the aqueous pulp from tank 12 into reaction column 14 via lines 22 and 26, and flow of oxygen through line 44 into diffuser 18. Readings are taken with oxygen analyzer 36 and helium analyzer 38 before flow of helium is commenced through helium line 46 to oxygen line 44. At some predetermined time, flow of helium in line 46 to line 44 is commenced and readings are taken from oxygen analyzer 36 and helium analyzer 38 at regular intervals, typically every minute, until steady state values for both helium and oxygen are obtained.

During the course of helium addition, the pulp flow, pulp consistency, oxygen flow and temperature of the pulp are noted, also at regular intervals.

After steady state conditions have been reached and the appropriate measurements taken, the helium flow is turned off and after sufficient time for venting of all the helium from the system, readings are taken again with oxygen analyzer 36 and helium analyzer 38, to verify that they are the same as before the commencement of the sampling.

The aqueous pulp in pulp tank 12 may contain entrained air which thus introduces nitrogen into the system as well as providing a part of the oxygen in the system including oxygen which is dissolved and non-dissolved oxygen detected by oxygen analyzer 36. In such case the vent gases will additionally include undissolved air.

As will be explained in the discussion of the results, it is possible to calculate the degree of air entrainment of the pulp as well as the oxygen utilized by the pulp in reaction column 14.

The sampling operation can conveniently be carried out at several different known oxygen rates to determine which is the most effective to meet the objectives of the particular mill system.

Essentially the same system 10 is employed in either an oxygen delignification stage or an oxygen extraction stage, the difference being essentially in the nature of the reaction column 14.

In the oxygen delignification system the reaction column 14 will be significantly larger than that in the oxygen extraction process so as to obtain a longer reaction time. In the case of the oxygen delignification process the retention time in column 14 is suitably 60 minutes ±15 minutes. In the case of the oxygen extraction process the retention time in reaction column 14 is by comparison about 10 minutes.

With respect to analyzers 36 and 38, such analyzers are available and are not the subject of the present invention. Suitable known oxygen analyzers include the paramagnetic oxygen analyzers in which the oxygen is subject to a magnetic field to which the oxygen responds.

Suitable helium analzyers 38 are known include analyzers which rely on the thermal conductivity of helium being significantly higher and different from that of oxygen, nitrogen and air, the other main components of the vent gas.

MEASUREMENTS AND CALCULATIONS

Figure 3:
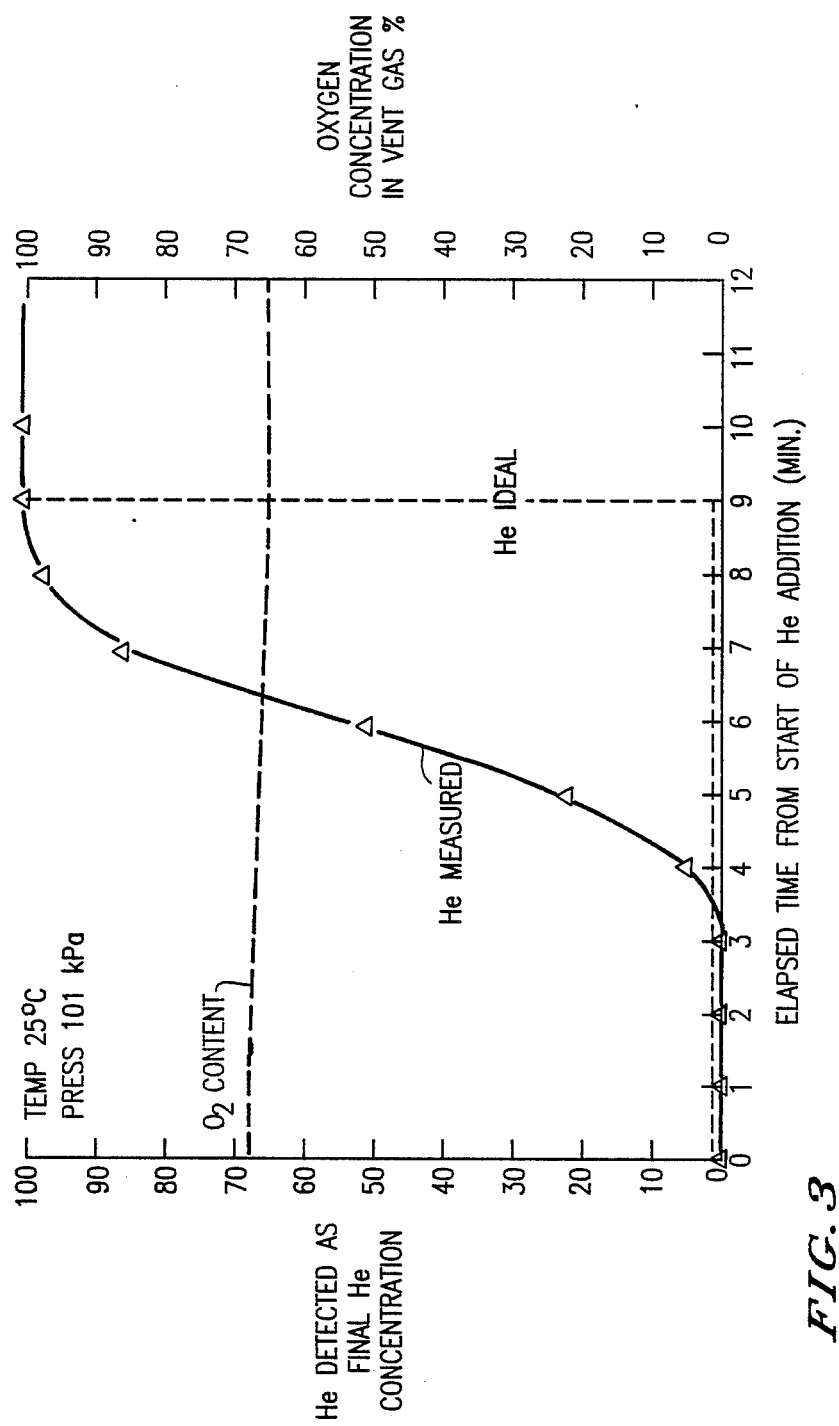
FIG. 3 shows graphically a vent gas plot.

The measurements of helium and oxygen concentration in sampling assembly 16 are plotted against time from the start of helium addition and a typical plot is shown in FIG. 3 where the helium concentration is expressed as a percentage of the final reading.

Examination of FIG. 3 indicates if there is channeling or bypassing of the gases in reaction column 14.

If the gas is well dispersed and held in the pulp in column 14, and if there is plug flow of the pulp upwardly in column 14, then helium will not be detected by helium analyzer 38 until the time elapsed after the first helium addition corresponds to the hydraulic residence time of the pulp required to reach sampling line 30. In such case, the helium concentration build up will follow the He IDEAL plot shown in FIG. 3.

In practice the helium will usually be detected sooner than this, indicating either channeling of the pulp, separation and channeling of the dispersed gas, or both conditions, and in practice the helium concentration is found to increase as shown by the He MEASURED curve in FIG. 3.

Figure 4:
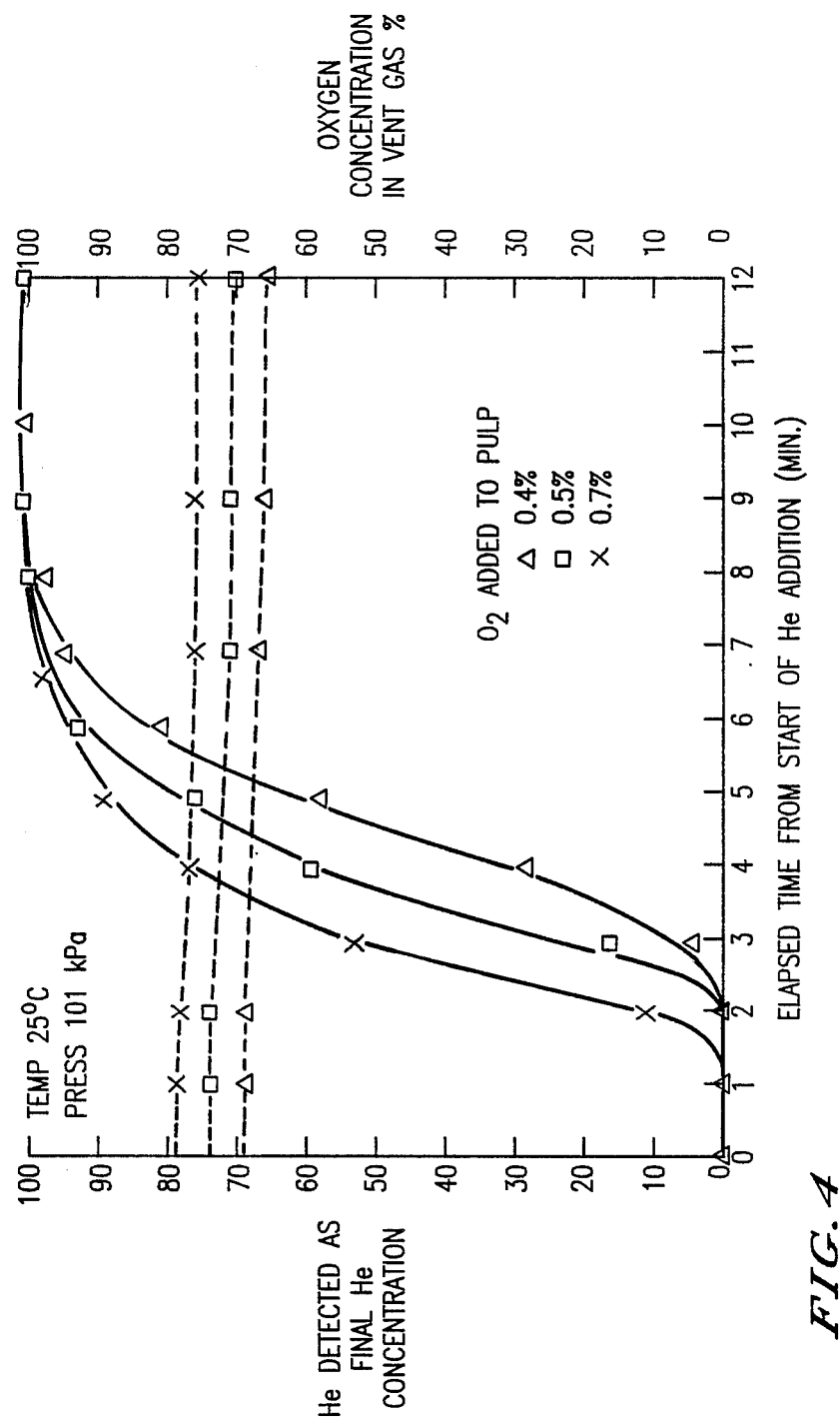
FIG. 4 demonstrates graphically the effect of different oxygen addition rates on the vent gas.

As more oxygen is added to the pulp, the channeling effect of gas or pulp or both becomes more pronounced as demonstrated by FIG. 4. Additionally, the oxygen content of the vent gas increases.

From the known flow rates of helium, gas and oxygen gas, respectively, introduced into the pulp and from the concentrations of helium and oxygen respectively in the vent gas measured by the sampling assembly 16, the following calculations can be made:

He flow rate = $Q_1$
$O_2$ flow rate = $Q_2$
He concentration in vent gas = $C_1$
$O_2$ concentration in vent gas = $C_2$ (i) Determine vent gas flow rate.

$$\text{vent gas flow rate} = \frac{100}{\text{He concentration \%}} \times \text{He flow rate}$$

$$\text{i.e. } \frac{100}{C_1} \times Q_1$$

(ii) Determine oxygen flow contained in vent gas flow rate.

$$O_2 \text{ flow rate} = \text{vent gas flow rate} \times O_2 \frac{\text{concentration \%}}{100}$$

$$\text{i.e. } \frac{100}{C_1} \times Q_1 \times \frac{C_2}{100} = \frac{C_2}{C_1} \times Q_1$$

(iii) Determine nitrogen flow rate.

nitrogen flow rate = vent gas flow rate − ($O_2$ flow rate + He flow rate)

$$\text{i.e. } \frac{100}{C_1} \times Q_1 - \left( \frac{C_2}{C_1} \times Q_1 + Q_1 \right) =$$

-continued $$\frac{Q_1}{C_1}(100 - (C_2 + C_1))$$

(iv) Determine air flow rate.
Since all the nitrogen present is derived from air, $$\text{air flow rate} = N_2 \frac{\text{flow rate} \times 100}{79}$$

i.e. $\frac{Q_1 \times 100}{C_1 \times 79}(100 - (C_2 + C_1))$ (v) Determine oxygen unreacted, assuming no oxygen is consumed from air.

Unreacted oxygen flow rate = vent gas flow rate − (air + He flow rate)

i.e. $\frac{100}{C_1} \times Q_1 - \left(\frac{Q_1 \times 100}{C_1 \times 79}(100 - (C_2 + C_1))\right) - Q_1$ (vi) Determine oxygen reacted:

oxygen flow rate reacted =

$O_2$ flow rate added to pulp − unreacted oxygen flow rate.

i.e. $Q_2 -$ $$\left[\frac{100 \times Q_1}{C_1} - \left(\frac{Q_1 \times 100}{C_1 \times 79}(100 - (C_2 + C_1))\right) - Q_1\right]$$

(vii) Percentage oxygen reacted =

$$\frac{O_2 \text{ flow rate reacted} \times 100}{O_2 \text{ flow rate added}}$$

i.e. $\dfrac{\left(Q_2 - \left[\dfrac{100 \times Q_1}{C_1} - \dfrac{Q_1 \times 100}{C_1 \times 79}(100 - (C_2 + C_1)) - Q_1\right]\right) \times 100}{Q_2}$ (viii) Percentage air in pulp =

$$\frac{\text{air flow rate}}{\text{pulp flow rate} + \text{air flow rate}} \times 100$$

Thus employing the method and system of the invention it is possible to determine the oxygen reacted and the percentage of air in the pulp and by reference to plots such as demonstrated by FIG. 3 it is possible to evaluate the separation or channeling in the reaction column 14.

Thus, not only can the procedure be employed to determine, for example, how much oxygen is absorbed and reacts in the oxygen delignification or oxygen extraction stages, it can also be used as a means to optimize oxygen addition to the pulp to ensure that the maximum benefit is obtained.

Similarly by examining the helium breakthrough curves such as illustrated in FIG. 3, it is possible to determine whether or not there is a gas channeling or pulp channeling or both in the reaction column.

Finally, it is possible to determine the air that is entrained by the pulp.

We claim:

1. In a method of treating an aqueous cellulosic pulp with oxygen in which a stream of oxygen gas is delivered to the pulp and oxygen is dispersed therein, the pulp with the oxygen is introduced into a reactor and the pulp is reacted with dispersed oxygen in the reactor, the improvement comprising:
   measuring the flow rate of the stream of oxygen gas,
   introducing an inert gas, at a known flow rate, into said stream of oxygen gas,
   removing a vent gas from said reactor, said vent gas comprising said inert gas and unreacted oxygen,
   measuring the concentration of said inert gas and the concentration of oxygen in said vent gas, and
   determining the oxygen gas consumption of the reactor from the measured parameters,
   said inert gas being essentially insoluble in said pulp and non-reacting in said reactor and having a property such that it can be determined in the presence of oxygen.

2. A method according to claim 1, in which said inert gas is helium.

3. A method according to claim 1, in which the pulp contains entrained air.

4. A method according to claim 2, in which the pulp contains entrained air.

5. A method of determining a gas parameter during oxygen gas consumption by an aqueous cellulosic pulp containing entrained air, in a reactor comprising:
   (i) continuously feeding a stream of aqueous cellulosic pulp containing entrained air into said reactor,
   (ii) providing a continuous stream of oxygen gas at a measured flow rate,
   (iii) continuously feeding an inert gas at a measured flow rate into said stream of oxygen gas to form a joint stream,
   (iv) feeding said joint stream into said stream of aqueous cellulosic pulp upstream of said reactor and dispersing oxygen of said joint stream in said pulp,
   (v) reacting components of said pulp with dispersed oxygen in said reactor,
   (vi) venting a vent gas comprising said inert gas, nitrogen from said entrained air and unreacted oxygen from said reactor,
   (vii) measuring parameters comprising the concentration of oxygen and the concentration of inert gas in said vent gas, and
   (viii) determining from the measured parameters at least one of:
      (a) oxygen gas consumption in said reactor,
      (b) air entrainment of said pulp, and
      (c) channeling in said reactor,
   said inert gas being essentially insoluble in said pulp and non-reacting in said reactor and having a property such that it can be determined in the presence of oxygen.

6. A method according to claim 5, in which said inert gas is helium.

* * * * *